United States Patent
Kaku et al.

(10) Patent No.: US 9,943,230 B2
(45) Date of Patent: Apr. 17, 2018

(54) ENDOSCOPE SYSTEM, PROCESSOR DEVICE OF ENDOSCOPE SYSTEM, AND IMAGE PROCESSING METHOD

(71) Applicant: FUJIFILM Corporation, Tokyo (JP)

(72) Inventors: Toshihiko Kaku, Ashigarakami-gun (JP); Takayuki Iida, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 807 days.

(21) Appl. No.: 14/321,116

(22) Filed: Jul. 1, 2014

(65) Prior Publication Data
US 2014/0316283 A1  Oct. 23, 2014

Related U.S. Application Data

(63) Continuation of application No. PCT/JP2013/050361, filed on Jan. 11, 2013.

(30) Foreign Application Priority Data

Jan. 25, 2012  (JP) .................................. 2012-013317

(51) Int. Cl.
*A61B 1/04*  (2006.01)
*A61B 5/00*  (2006.01)
(Continued)

(52) U.S. Cl.
CPC ........ *A61B 5/0084* (2013.01); *A61B 1/00009* (2013.01); *A61B 1/043* (2013.01);
(Continued)

(58) Field of Classification Search
CPC .......... A61B 1/05; A61B 1/063; A61B 5/0084
See application file for complete search history.

(56) References Cited

U.S. PATENT DOCUMENTS

| 2011/0077462 A1* | 3/2011 | Saitou | A61B 1/0638 600/109 |
|---|---|---|---|
| 2012/0327205 A1 | 12/2012 | Takahashi | |
| 2013/0289373 A1* | 10/2013 | Yamamoto | A61B 1/0638 600/339 |

FOREIGN PATENT DOCUMENTS

| EP | 2 301 416 A1 | 3/2011 |
|---|---|---|
| EP | 2 305 094 A1 | 4/2011 |
| EP | 2 368 480 A1 | 9/2011 |
| JP | 2011-135983 A | 7/2011 |

OTHER PUBLICATIONS

Extended European Search Report dated Mar. 17, 2016 in corresponding European Application No. 13741638.4.
(Continued)

*Primary Examiner* — Michael D Abreu
(74) *Attorney, Agent, or Firm* — Birch, Stewart, Kolasch & Birch, LLP

(57) ABSTRACT

Even if the ratio between blue and green components of illumination light is changed, a plurality of types of blood vessels at different depths are reliably distinguished. A blue signal B, a green signal G, a red signal R is obtained by imaging the subject using a color CCD 44. A B/G image having a B/G ratio is generated. A superficial blood vessel extraction image is obtained by extracting a pixel, in which the B/G ratio is equal to or less than a boundary value Ls between the mucous membrane and the superficial blood vessel, from the B/G image. A medium-deep blood vessel extraction image is obtained by extracting a pixel, in which the B/G ratio is equal to or greater than a boundary value Ld between the mucous membrane and the medium-deep blood vessel. The boundary values Ls and Ld differ depending on the light amount ratio.

20 Claims, 22 Drawing Sheets

(51) Int. Cl.
  *A61B 1/00* (2006.01)
  *G06T 7/00* (2017.01)
  *A61B 5/02* (2006.01)
  *G06K 9/00* (2006.01)
  *G06T 11/00* (2006.01)
  *G06T 7/90* (2017.01)
  *A61B 1/06* (2006.01)

(52) U.S. Cl.
  CPC .......... *A61B 1/0638* (2013.01); *A61B 1/0646* (2013.01); *A61B 1/0653* (2013.01); *A61B 5/02007* (2013.01); *G06K 9/0014* (2013.01); *G06T 7/0012* (2013.01); *G06T 7/90* (2017.01); *G06T 11/001* (2013.01); *A61B 1/0005* (2013.01); *A61B 1/063* (2013.01); *G06T 2207/10024* (2013.01); *G06T 2207/10068* (2013.01); *G06T 2207/10152* (2013.01); *G06T 2207/30101* (2013.01)

(56) References Cited

OTHER PUBLICATIONS

International Search Report, dated Apr. 9, 2013, issued in PCT/JP2013/050361.
Written Opinion of the International Searching Authority, dated Apr. 9, 2013, issued in PCT/JP2013/050361.

* cited by examiner

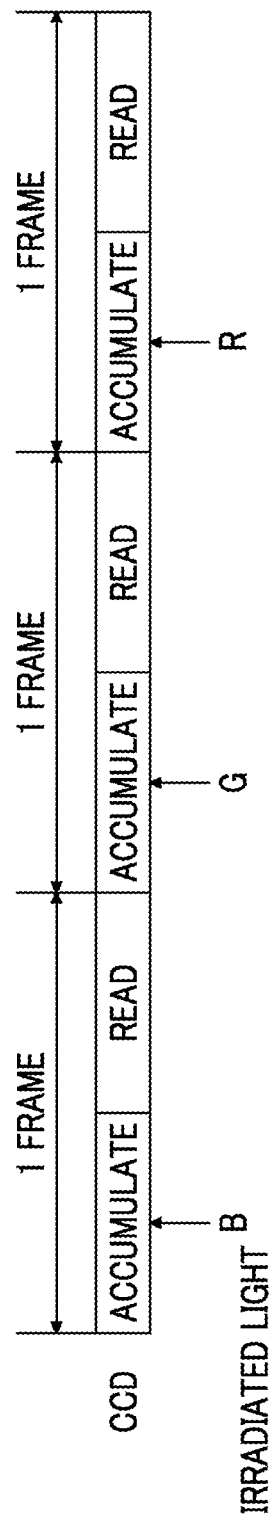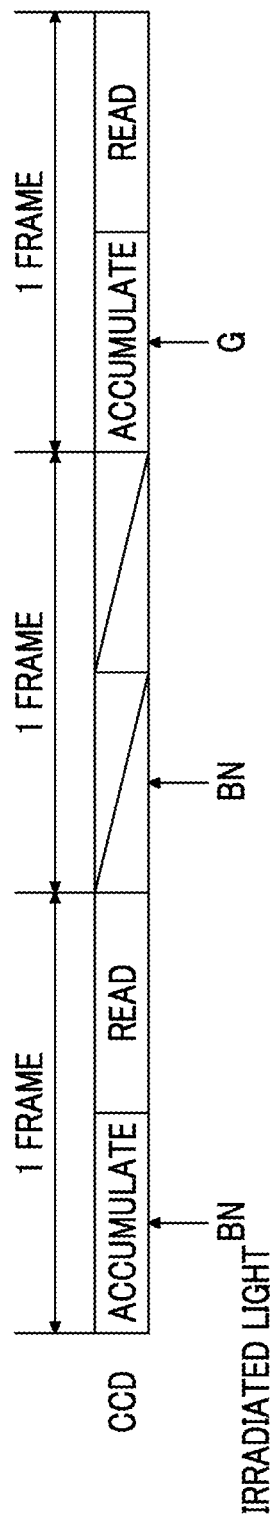

ENDOSCOPE SYSTEM, PROCESSOR DEVICE OF ENDOSCOPE SYSTEM, AND IMAGE PROCESSING METHOD

CROSS-REFERENCE TO RELATED APPLICATIONS

This application is a Continuation of PCT International Application No. PCT/JP2013/050361 filed on Jan. 11, 2013, which claims priority under 35 U.S.C. § 119(a) to Japanese Patent Application No. 2012-013317 filed Jan. 25, 2012. Each of the above applications is hereby expressly incorporated by reference, in its entirety, into the present application.

BACKGROUND OF THE INVENTION

1. Field of the Invention

The present invention relates to an endoscope system capable of extracting blood vessels, such as superficial blood vessels and medium-deep blood vessels, from a subject, a processor device of the endoscope system, and an image processing method.

2. Description of the Related Art

In recent medical treatment, diagnosis or the like using an endoscope apparatus has been widely performed. As observation of the inside of a subject using an endoscope apparatus, not only normal observation to observe the subject's inside in its entirety but also special observation to observe a specific part on the subject when the specific part needs to be enhanced has been performed.

In the aforementioned special observation, determination regarding whether or not cancer is present from the shape of a highlighted blood vessel is performed. Types of blood vessels mainly include superficial blood vessels distributed on a living tissue surface and medium-deep blood vessels located below the superficial blood vessels. Depending on the purpose of diagnosis, diagnosis may be performed focusing on certain blood vessels. In this case, if blood vessels that are not the focus of observation are added in an endoscope image, diagnosis may be interrupted by the blood vessel. For this reason, differentiating superficial blood vessels or medium-deep blood vessels from the image and displaying an image, which is obtained by extracting only blood vessels to be observed, on a monitor has been demanded.

Regarding the method of determining the depth of a blood vessel, JP2011-135983A discloses a method of performing determination as a superficial blood vessel when the hue of a narrowband image generated based on narrowband light in a specified wavelength region (415 nm, 540 nm) is 5 to 35 and performing determination as a medium-deep blood vessel when the hue is 170 to 200.

SUMMARY OF INVENTION

In recent years, a semiconductor light source, such as a laser light source, has become used as an illumination light source used for normal observation and special observation. For example, in the normal observation, a subject is illuminated with fluorescent light (green to red) that is excited and emitted by irradiating a phosphor with first blue laser light having a center wavelength of 405 nm and second blue laser light having a center wavelength of 445 nm. In the special observation, the ratio between the components of respective colors of illumination light is also changed by adjusting the light amount ratio between the first blue laser light and the second blue laser light. Since the degree of penetration of illumination light into the living tissue has a wavelength dependency, it is possible to change a part to be made clear. For example, when the percentage of a blue component of illumination light is larger than the percentage of a green component by adjusting the light amount ratio, a superficial blood vessel can be made clear. On the contrary, when the green component is larger than the blue component, a medium-deep blood vessel can be made clear.

Thus, a blood vessel to be observed can be made clear by adjusting the light amount ratio. However, some blood vessels that are not to be observed are slightly displayed although not noticeable. The aforementioned slightly displayed blood vessels reduce the visibility of a blood vessel to be observed. Therefore, it is necessary to distinguish and extract only a blood vessel to be observed. However, if the light amount ratio is adjusted, the hue on the image is changed. For this reason, in the blood vessel discrimination method based on the hue disclosed in JP2011-135983A it is not possible to reliably extract a blood vessel to be observed.

The present invention has been made in view of the above-background, and it is an object of the present invention to provide an endoscope system capable of reliably extracting a plurality of types of blood vessels at different depths even if the ratio between blue and green components of illumination light irradiated to a subject is changed, a processor device of the endoscope system, and an image processing method.

In order to achieve the above-described object, an endoscope system of the present invention includes: an illumination unit that includes a light emitting unit, which emits two or more illumination light beams including first illumination light and second illumination light having different wavelength regions, and a light amount ratio setting unit, which sets a light amount ratio between the first illumination light and the second illumination light, and that irradiates a subject with the first illumination light and the second illumination light based on the light amount ratio set by the light amount ratio setting unit; an image signal acquisition unit for acquiring two or more color signals having different pieces of color information by receiving and imaging return light from the subject using an imaging element; a multi-color image generation unit for generating a multi-color image formed from calculated values obtained by performing predetermined calculation for each pixel using the two or more color signals; and a blood vessel extraction image generation unit for generating at least one of a first layer blood vessel extraction image, which is obtained by extracting a first layer blood vessel at a specific depth from the multi-color image, and a second layer blood vessel extraction image, which is obtained by extracting a second layer blood vessel at a position deeper than the first layer blood vessel from the multi-color image, by performing blood vessel extraction processing, which differs depending on the light amount ratio, on the multi-color image.

Preferably, the light amount ratio setting unit sets one of a plurality of light amount ratios set in advance, and the blood vessel extraction image generation unit includes a plurality of calculated value tables, which are set for the plurality of light amount ratios and which store a correlation between a mucous membrane, the first layer blood vessel, and the second layer blood vessel of the subject and the calculated values, and a blood vessel extraction image generation unit that generates at least one of the first layer blood vessel extraction image and the second layer blood vessel extraction image by performing blood vessel extraction processing using a calculated value table corresponding to the light amount ratio set by the light amount ratio setting unit.

Preferably, in each of the calculated value tables, a calculated value indicating a boundary between the mucous membrane and the first layer blood vessel is stored as a first boundary value, and a calculated value indicating a boundary between the mucous membrane and the second layer blood vessel is stored as a second boundary value. Preferably, the first and second boundary values differ depending on each calculated value table.

It is preferable to further include a blood vessel enhancement image or suppression image generation unit for generating a first layer blood vessel enhancement image or suppression image, in which the first layer blood vessel is enhanced or suppressed, using the first layer blood vessel extraction image or generating a second layer blood vessel enhancement image or suppression image, in which the second layer blood vessel is enhanced or suppressed, using the second layer blood vessel extraction image. It is preferable to further include a display unit for displaying at least one of the first layer blood vessel enhancement image or suppression image and the second layer blood vessel enhancement image or suppression image.

Preferably, the illumination unit irradiates first illumination light, which includes blue excitation light and fluorescent light that is wavelength-converted by a wavelength conversion member using the blue excitation light, and second illumination light, which has a wavelength region in which a center wavelength is on a short wavelength side compared with the excitation light, simultaneously toward the subject. Preferably, the image signal acquisition unit images the subject, to which the first illumination light and the second illumination light are irradiated simultaneously, using a color imaging element.

Preferably, the wavelength conversion member is provided in a separate light source device from an endoscope that irradiates the first illumination light and the second illumination light toward the subject. Preferably, the wavelength conversion member is provided at a distal end of an endoscope that irradiates the first illumination light and the second illumination light toward the subject. Preferably, a center wavelength of the excitation light is 445 nm, and a center wavelength of the second illumination light is 405 nm. Preferably, the first illumination light is illumination light having a center wavelength of 420 nm, and the second illumination light is illumination light having a center wavelength of 530 nm. Preferably, the color signals include a blue signal having information of a blue component and a green signal having information of a green component, and the multi-color image is a B/G image having a B/G ratio obtained by dividing the blue signal by the green signal for each pixel. In addition, the center wavelength 420 nm of the first illumination light is intended to include a range in which a center wavelength is 420 nm±5 nm, and the center wavelength 530 nm of the second illumination light is intended to include a range in which a center wavelength is 530 nm±5 nm.

Other aspect of the present invention is a processor device of an endoscope system including an illumination unit, which includes a light emitting unit that emits two or more illumination light beams including first illumination light and second illumination light having different wavelength regions and a light amount ratio setting unit that sets a light amount ratio between the first illumination light and the second illumination light and which irradiates a subject with the first illumination light and the second illumination light based on the light amount ratio set by the light amount ratio setting unit, and an electronic endoscope for acquiring two or more color signals having different pieces of color information by receiving and imaging return light from the subject using an imaging element. The processor device of an endoscope system includes: a multi-color image generation unit for generating a multi-color image formed from calculated values obtained by performing predetermined calculation for each pixel using the two or more color signals; and a blood vessel extraction image generation unit for generating at least one of a first layer blood vessel extraction image, which is obtained by extracting a first layer blood vessel at a specific depth from the multi-color image, and a second layer blood vessel extraction image, which is obtained by extracting a second layer blood vessel at a position deeper than the first layer blood vessel from the multi-color image, by performing blood vessel extraction processing, which differs depending on the light amount ratio, on the multi-color image.

Other aspect of the present invention is an image processing method performed in an endoscope system including an illumination unit, which includes a light emitting unit that emits two or more illumination light beams including first illumination light and second illumination light having different wavelength regions and a light amount ratio setting unit that sets a light amount ratio between the first illumination light and the second illumination light and which irradiates a subject with the first illumination light and the second illumination light based on the light amount ratio set by the light amount ratio setting unit, and an electronic endoscope for acquiring two or more color signals having different pieces of color information by receiving and imaging return light from the subject using an imaging element. The image processing method includes: generating a multi-color image formed from calculated values obtained by performing predetermined calculation for each pixel using the two or more color signals; and generating at least one of a first layer blood vessel extraction image, which is obtained by extracting a first layer blood vessel at a specific depth from the multi-color image, and a second layer blood vessel extraction image, which is obtained by extracting a second layer blood vessel at a position deeper than the first layer blood vessel from the multi-color image, by performing blood vessel extraction processing, which differs depending on the light amount ratio, on the multi-color image.

According to the present invention, since blood vessel extraction processing, which differs depending on the light amount ratio of the first illumination light and the second illumination light to illuminate a subject, is performed, it is possible to reliably extract a plurality of types of blood vessels at different depths even if the light amount ratio is changed.

BRIEF DESCRIPTION OF THE DRAWINGS

FIG. 19A is a diagram for explaining the imaging control in a normal observation mode, and FIG. 19B is a diagram for explaining the imaging control in first to third special observation modes.

DESCRIPTION OF THE PREFERRED EMBODIMENTS

Figure 1:
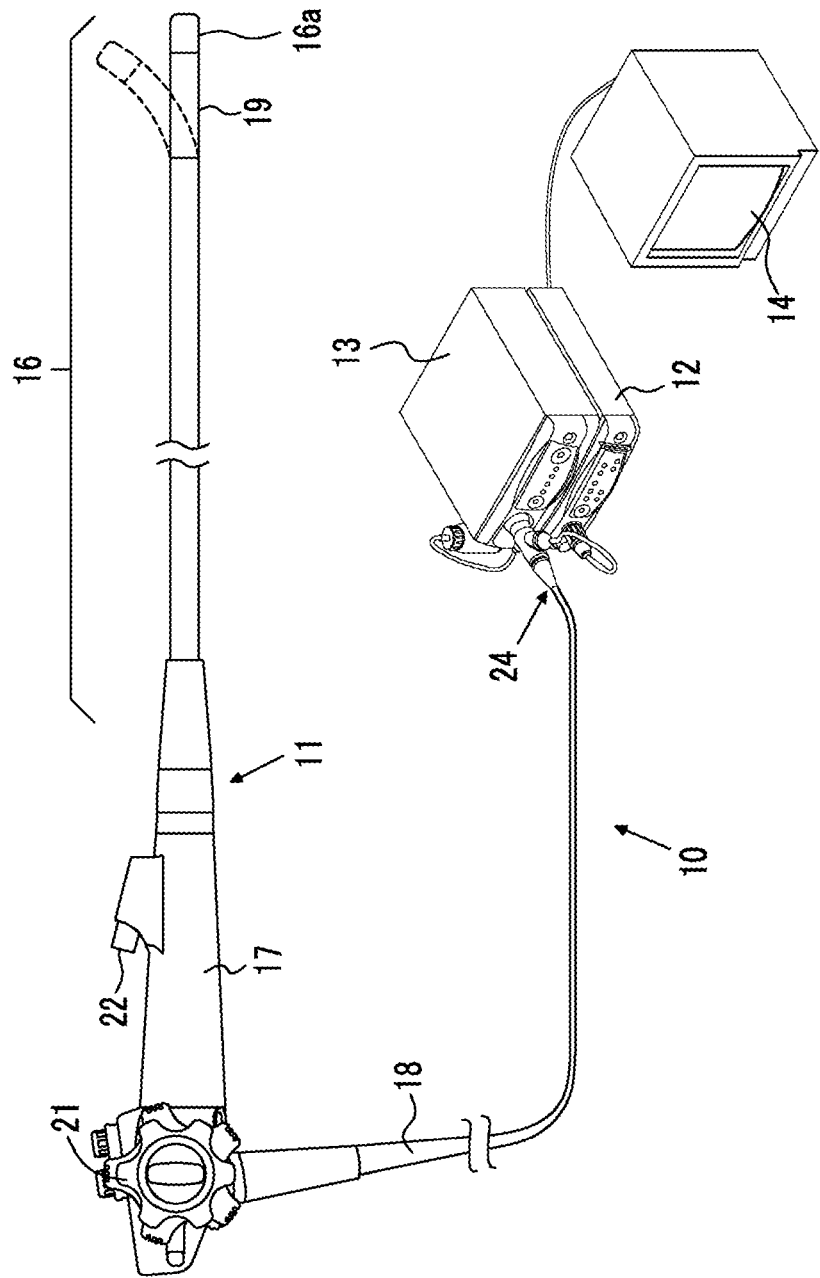
FIG. 1 is an external view of an electronic endoscope system.

As shown in FIG. 1, an electronic endoscope system 10 includes an electronic endoscope 11 that images the inside of a subject, a processor device 12 that generates an endoscope image based on a signal obtained by imaging, a light source device 13 that generates light for illuminating the subject, and a monitor 14 that displays an endoscope image. The electronic endoscope 11 includes a flexible insertion unit 16 that is inserted into the body cavity, an operating unit 17 provided at the proximal end of the insertion unit 16, and a universal code 18 that makes a connection between the operating unit 17 and the processor device 12 and the light source device 13.

The electronic endoscope system 10 has a function of generating a superficial blood vessel enhancement image or suppression image, in which a superficial blood vessel of a subject is enhanced/suppressed, and a medium-deep blood vessel enhancement image or suppression image, in which a medium-deep superficial blood vessel is enhanced/suppressed. Which blood vessel enhancement image or suppression image is to be generated is determined by the operation of a superficial layer and medium-deep layer selection SW 28 (refer to FIG. 2). The electronic endoscope system 10 has three observation modes of a first observation mode in which the inside of the subject is observed with illumination light in which the percentage of the blue component is approximately the same as the percentage of the green component, a second observation mode in which the inside of the subject is observed with illumination light in which the percentage of the blue component is larger than the percentage of the green component, and a third observation mode in which the inside of the subject is observed with illumination light in which the percentage of the green component is larger than the percentage of the blue component. The first to third observation modes are switched by an observation mode selection SW 29 (refer to FIG. 2).

A curved portion 19 obtained by connecting a plurality of curved pieces is formed at the distal end of the insertion unit 16. The curved portion 19 is curved in the horizontal and vertical directions by operating an angle knob 21 of the operating unit. A distal portion 16a including an optical system for imaging the body cavity and the like is provided at the distal end of the curved portion 19. The distal portion 16a is directed in a desired direction within the body cavity by the bending operation of the curved portion 19.

A connector 24 is attached to the universal code 18 on the side of the processor device 12 and the light source device 13. The connector 24 is a composite connector including a communication connector and a light source connector, and the electronic endoscope 11 is detachably connected to the processor device 12 and the light source device 13 through the connector 24.

Figure 2:
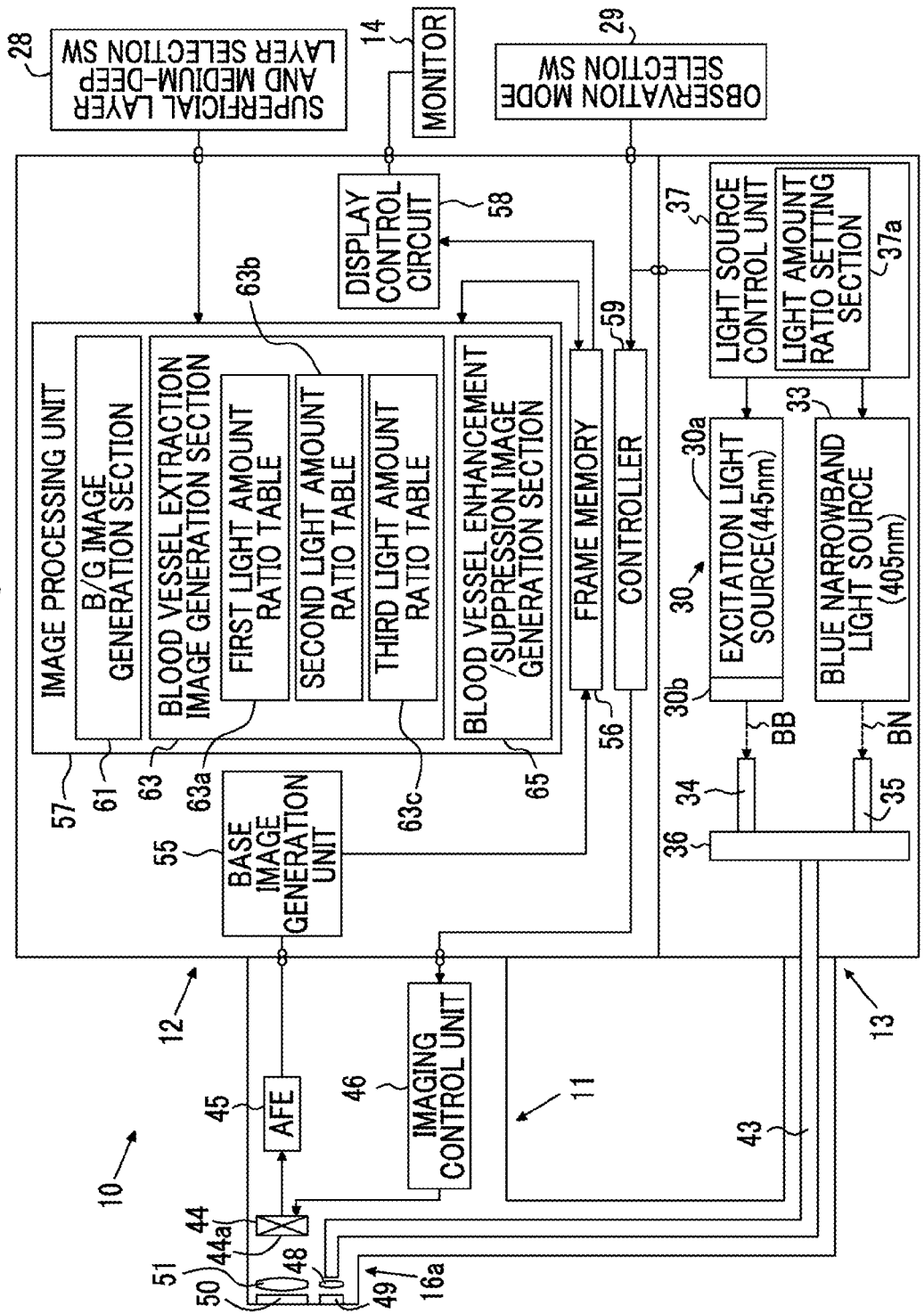
FIG. 2 is a block diagram showing the electrical configuration of the electronic endoscope system.

As shown in FIG. 2, the light source device 13 (a form of an illumination unit) includes a broadband light source 30, a blue narrowband light source 33, a coupler 36, and a light source control unit 37. The broadband light source 30 includes an excitation light source 30a that emits excitation light having a center wavelength of 445 nm and a phosphor 30b that is excited to emit fluorescent light of green to red due to the excitation light from the excitation light source 30a. The excitation light source 30a is a semiconductor light source, such as a light emitting diode (LED) or a laser diode (LD). As the excitation light source 30a, a broad area type InGaN-based laser diode can be used. In addition, an InGaNAs-based laser diode, a GaNAs-based laser diode, or the like can also be used.

Figure 3:
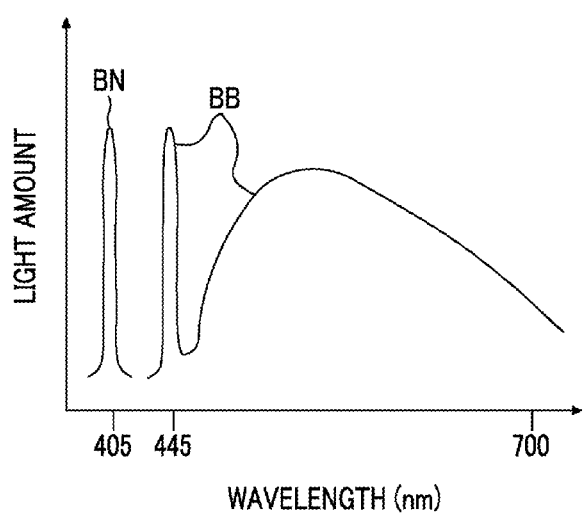
FIG. 3 is a graph showing the emission spectra of excitation light having a center wavelength of 445 nm, emitted excitation light that is excited and emitted by applying excitation light to a phosphor, and blue laser light having a center wavelength of 405 nm.

The phosphor 30b is configured to contain a plurality of kinds of fluorescent materials (for example, a YAG-based fluorescent material or a fluorescent material, such as BAM ($BaMgAl_{10}O_{17}$)) that absorb a part of excitation light and are excited to emit light of green to red. Accordingly, by combining the emitted excitation light (fluorescent light) of green to red emitted from the phosphor 30b with excitation light that is transmitted through the phosphor 30b without being absorbed by the phosphor 30b, white light BB (pseudo white light) having an emission spectrum shown in FIG. 3 is generated. The generated white light BB is incident on a broadband optical fiber 34.

It is preferable that the phosphor 30b have an approximately rectangular parallelepiped shape. In this case, the phosphor 30b may be formed by solidifying a phosphor material in an approximately rectangular parallelepiped shape using a binder, or may be formed in an approximately rectangular parallelepiped shape by mixing a phosphor material with resin, such as inorganic glass. The phosphor 30b is also referred to as a Micro White (MW; registered trademark) as a product name.

The blue narrowband light source 33 is a light emitting diode (LED), a laser diode (LD), or the like. As shown in FIG. 3, the blue narrowband light source 33 generates blue narrowband light BN having a limited wavelength of 400±10 nm (center wavelength of 405 nm). The blue narrowband light BN emitted from the blue narrowband light source 33 is incident on a narrowband optical fiber 35.

The coupler 36 connects a light guide 43 in the electronic endoscope 11 to the broadband optical fiber 34 and the narrowband optical fiber 35. Therefore, both the white light BB and the blue narrowband light BN are simultaneously incident on the light guide 43.

The light source control unit 37 controls the light amount of the excitation light source 30a and the blue narrowband light source 33 to maintain the light amount ratio of the white light BB and the blue narrowband light BN constant. The light amount ratio is set by a light amount ratio setting section 37a. Since the light amount ratio is set in advance for each of the first to third observation modes, the light amount ratio setting section 37a sets a light amount ratio corresponding to the observation mode selected by the observation mode selection SW 29. The first light amount ratio in the first observation mode is set such that the percentage of the blue component of the illumination light irradiated to the subject is approximately the same as the percentage of the green component of the illumination light. When the inside of the subject is illuminated in the first light amount ratio, the subject's inside in its entirety can be brightened, and a portion distributed on the surface, such as a superficial blood vessel, can be made clear.

The second light amount ratio in the second observation mode is set such that the percentage of the blue component of the illumination light is larger than the percentage of the green component of the illumination light. When the inside of the subject is illuminated in the second light amount ratio, both the superficial blood vessel and the medium-deep blood vessel can be made clear. The third light amount ratio in the third observation mode is set such that the percentage of the green component of the illumination light is larger than the percentage of the blue component of the illumination light. When the inside of the subject is illuminated in the third light amount ratio, it is possible to brighten the the subject's inside in its entirety. In addition, when the third light amount ratio is set, it is preferable that the light amount of the blue narrowband light BN be set to about 10% of the maximum light amount.

The electronic endoscope 11 includes the light guide 43, a CCD 44, an analog processing circuit 45 (analog front end: AFE), and an imaging control unit 46. The light guide 43 is a large-diameter optical fiber, a bundle fiber, or the like, and the incidence end is inserted into the coupler 36 in the light source device and the exit end is directed toward an irradiation lens 48 provided in the distal portion 16a. The white light BB and the blue narrowband light BN guided by the light guide 43 are irradiated into the subject through the irradiation lens 48 and an illumination window 49 attached to the end surface of the distal portion 16a. The white light BB and the blue narrowband light BN reflected within the subject are incident on a condensing lens 51 through an observation window 50 attached to the end surface of the distal portion 16a.

The CCD 44 receives light from the condensing lens 51 through an imaging surface 44a, performs photoelectric conversion of the received light and accumulates signal charges, and reads the accumulated signal charges as an imaging signal. The read imaging signal is transmitted to an AFE 45. The CCD 44 is a color CCD, and pixels of three colors of a B pixel in which a color filter of B color is provided, a G pixel in which a color filter of G color is provided, and an R pixel in which a color filter of R color is provided are arrayed on the imaging surface 44a. For the CCD 44, it is preferable to adopt the Bayer array in which the ratio of B, and R pixels is 1:2:1. A form of an image signal acquisition unit is configured to include the condensing lens 51, the CCD 44 having the imaging surface 44a, and the AFE 45.

Figure 4:
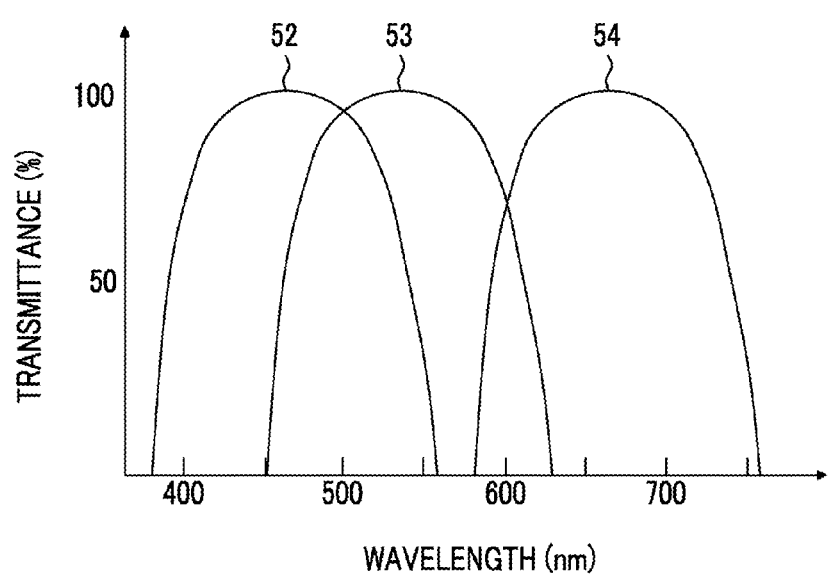
FIG. 4 is a graph showing the spectral transmittances of color filters of R, G, and B colors.

The color filters of B, G, and R colors have transmission distributions 52, 53, and 54, respectively, as shown in FIG. 4. When only the white light BB having a wavelength region of about 400 nm to 700 nm is incident on the CCD 44, the color filters of B, G, and R colors allow light having a wavelength corresponding to the transmission distributions 52, 53, and 54, of the white light BB, to be transmitted therethrough. Here, it is assumed that a signal photoelectrically converted by the R pixel is a red signal R, a signal photoelectrically converted by the G pixel is a green signal G, and a signal photoelectrically converted by the B pixel is a blue signal B.

The AFE 45 is configured to include a correlated double sampling circuit (CDS), an automatic gain control circuit (AGC), and an analog/digital converter (A/D) (all not shown). The CDS performs correlated double sampling processing on an imaging signal from the CCD 44 to remove noise caused by the driving of the CCD 44. The AGC amplifies an imaging signal from which noise has been removed by the CDS. The A/D converts an imaging signal amplified by the AGC into a digital imaging signal of a predetermined number of bits, and inputs the digital imaging signal to the processor device 12.

The imaging control unit 46 is connected to a controller 59 in the processor device 12, and transmits a driving signal to the CCD 44 when there is an instruction from the controller 59. The CCD 44 outputs an imaging signal to the AFE 45 at a predetermined frame rate based on the driving signal from the imaging control unit 46.

As shown in FIG. 2, the processor device 12 includes a base image generation unit 55, a frame memory 56, an image processing unit 57, and a display control circuit 58. The controller 59 controls each of the units. The base image generation unit 55 generates a base image by performing various kinds of signal processing on the blue signal B, the green signal G, and the red signal R output from the AFE 45 of the electronic endoscope. The generated base image is temporarily stored in the frame memory 56. The blue signal B, the green signal G, and the red signal R output from the AFE 45 are stored in the frame memory 56. The base image may be a pseudo color image obtained by pseudo coloring of blood vessel function information, such as oxygen saturation.

The image processing unit 57 includes a B/G image generation section 61 (a form of a multi-color image generation unit), a blood vessel extraction image generation section 63, and a blood vessel enhancement image or suppression image generation section 65 (a form of a blood vessel enhancement image or suppression image generation unit). The B/G image generation section 61 generates a B/G image having a brightness ratio B/G (B/G ratio) between the blue signal B and the green signal G. Here, the B/G ratio indicates a brightness ratio of pixels at the same position between the blue signal B and the green signal G.

Figure 5:
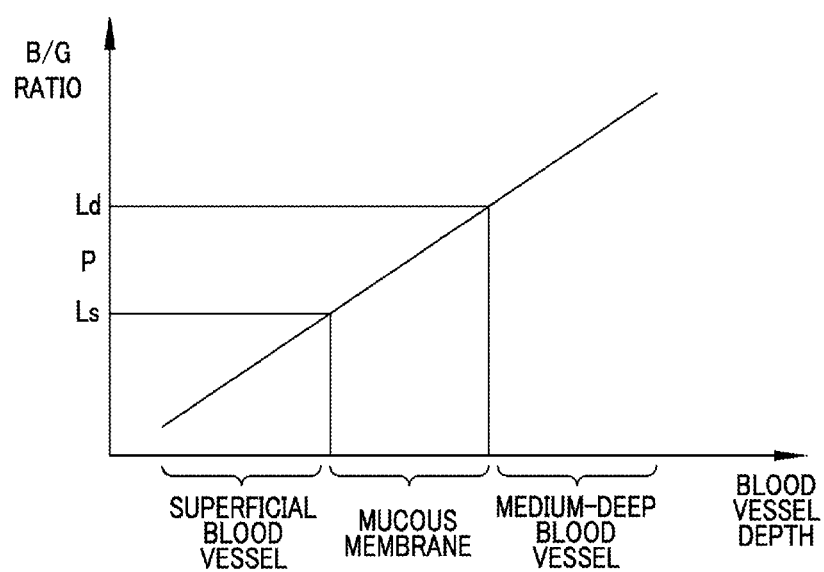
FIG. 5 is a graph showing the relationship between the blood vessel depth and the B/G ratio that is stored in a first light amount ratio table.

The blood vessel extraction image generation section 63 generates a superficial blood vessel extraction image by extracting the superficial blood vessel based on the B/G image, or generates a medium-deep blood vessel extraction image by extracting the medium-deep blood vessel based on the B/G image. The method of generating the blood vessel extraction images differs depending on which of the first to third observation modes is set. When the first observation mode is set, a superficial blood vessel extraction image or a medium-deep blood vessel extraction image is generated using a first light amount ratio table 63a that is suitable for the first light amount ratio in the first observation mode. Correlation between the brightness ratio B/G and the blood vessel depth shown in FIG. 5 is stored in the first light amount ratio table 63a. This correlation is a proportional relationship in which the brightness ratio B/G (B/G ratio) increases as the blood vessel depth increases. In addition, a form of a blood vessel extraction image generation unit is configured to include a blood vessel extraction image generation section 63 and the first light amount ratio table 63a to a third light amount ratio table 63c.

Figure 6:
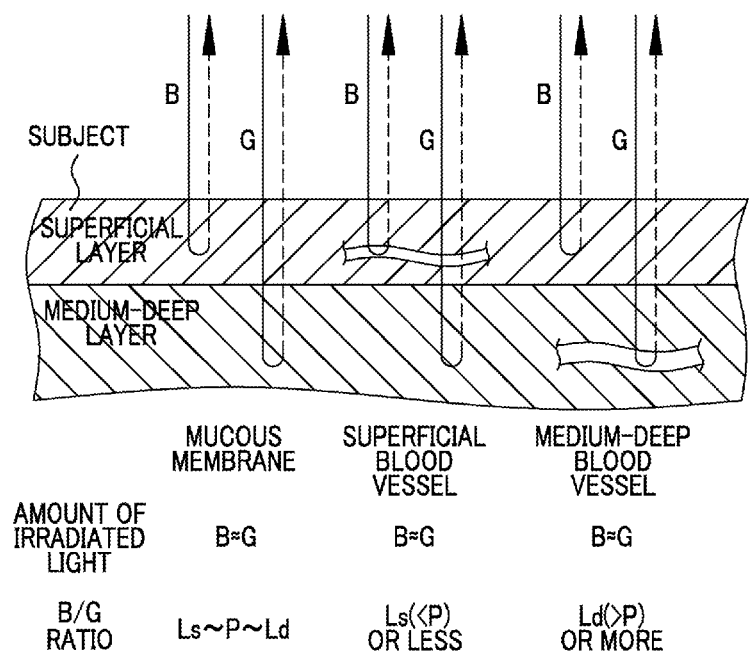
FIG. 6 is a diagram for explaining the B/G ratio when illumination light, in which the percentages of the B and G components are approximately the same, is irradiated to the mucous membrane, the superficial blood vessel, and the medium-deep blood vessel.

In the first observation mode, the percentage of the blue component (B component) of the illumination light is approximately the same as the percentage of the green component (G component) of the illumination light. Therefore, as shown in FIG. 6, when the illumination light is irradiated to the mucous membrane with no blood vessels, the ratio of the B and G components of the return light is approximately fixed. This is because there is no large light absorption in the mucous membrane. Assuming that the average B/G ratio in this case is P, the B/G ratio in the mucous membrane falls within a fixed range of "Ls to P to Ld". Here, Ls is a lower limit of the B/G ratio of the mucous membrane in the first observation mode, and Ld is an upper limit of the B/G ratio of the mucous membrane in the first observation mode.

When illumination light is irradiated to a superficial blood vessel, the B component of the illumination light is largely absorbed by the superficial blood vessel, while the G component is not absorbed almost. For this reason, the B/G ratio is equal to or less than Ls in most cases. Therefore, it can be seen that the superficial blood vessel is projected to the pixel having a B/G ratio equal to or less than Ls (that is, Ls is a boundary value between the mucous membrane and the superficial blood vessel). On the other hand, when illumination light is irradiated to a medium-deep blood vessel, the G component of the illumination light is largely absorbed by the medium-deep blood vessel, while the B component is not absorbed almost. For this reason, the B/G ratio is equal to or greater than Ld in most cases. Therefore, it can be seen that the medium-deep blood vessel is projected to the pixel having a B/G ratio equal to or larger than Ld (that is, Ld is a boundary value between the mucous membrane and the medium-deep blood vessel).

Accordingly, when generating a superficial blood vessel extraction image in the first observation mode, only the pixel value of a pixel having a B/G ratio equal to or less than Ls is extracted from the B/G image, and binarization processing for setting the pixel values of other pixels to 0 is performed. On the other hand, when generating a medium-deep blood vessel extraction image, only the pixel value of a pixel having a B/G ratio equal to or greater than Ld is extracted from the B/G image, and binarization processing for setting the pixel values of other pixels to 0 is performed.

Figure 7:
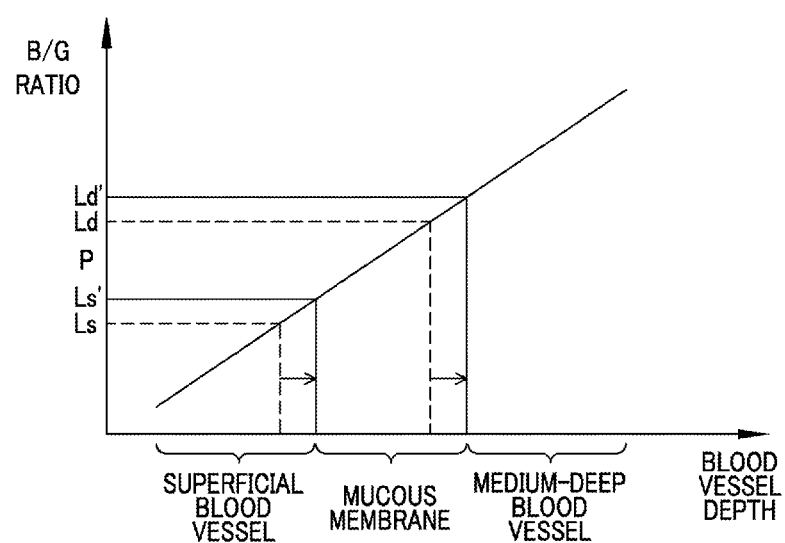
FIG. 7 is a graph showing the relationship between the blood vessel depth and the B/G ratio that is stored in a second light amount ratio table.
Figure 8:
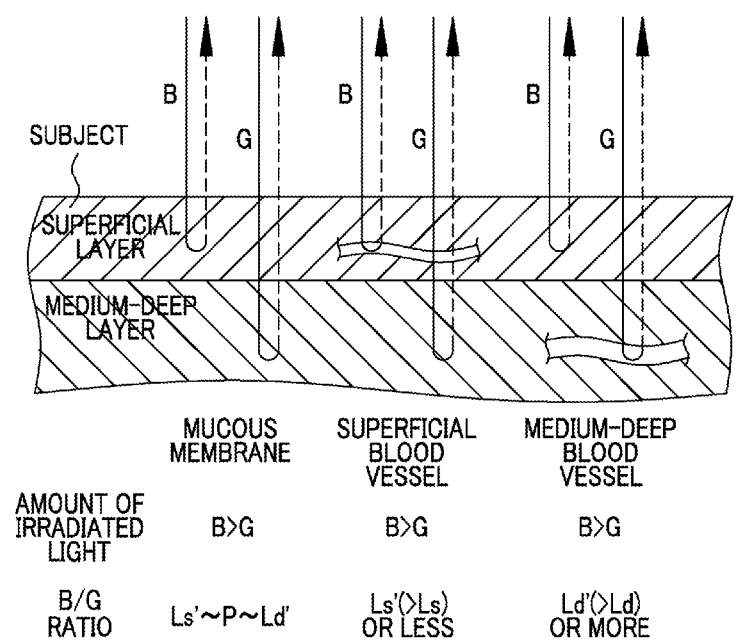
FIG. 8 is a diagram for explaining the B/G ratio when illumination light, in which the percentage of the B component is larger than the percentage of the G component, is irradiated to the mucous membrane, the superficial blood vessel, and the medium-deep blood vessel.

When the second observation mode is set, a superficial blood vessel extraction image or a medium-deep blood vessel extraction image is generated using a second light amount ratio table 63b that is suitable for the second light amount ratio in the second observation mode. As shown in FIG. 7, similar to the first light amount ratio table 63a, the second light amount ratio table 63b shows a proportional relationship in which the brightness ratio B/G (B/G ratio) increases as the blood vessel depth increases. In the second observation mode, as shown in FIG. 8, since the percentage of the blue wavelength component (B component) of the illumination light is larger than the percentage of the green wavelength component (G component) of the illumination light, the B/G ratio is generally high. Accordingly, a boundary value Ls' between the mucous membrane and the superficial blood vessel is larger than the boundary value Ls in the first observation mode, and a boundary value Ld' between the mucous membrane and the medium-deep blood vessel is larger than the boundary value Ld in the first observation mode.

Therefore, when generating a superficial blood vessel extraction image in the second observation mode, only the pixel value of a pixel having a B/G ratio equal to or less than Ls' is extracted from the B/G image, and binarization processing for setting the pixel values of other pixels to 0 is performed. On the other hand, when generating a medium-deep blood vessel extraction image, only the pixel value of a pixel having a B/G ratio equal to or greater than Ld' is extracted from the B/G image, and binarization processing for setting the pixel values of other pixels to 0 is performed.

Figure 9:
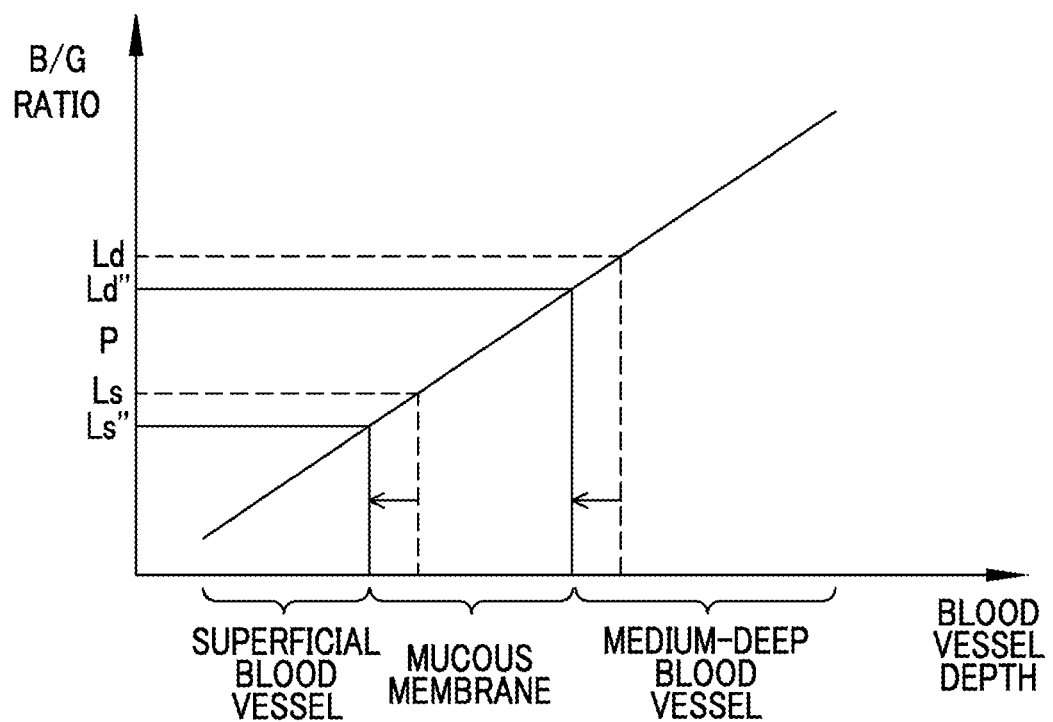
FIG. 9 is a graph showing the relationship between the blood vessel depth and the B/G ratio that is stored in a third light amount ratio table.
Figure 10:
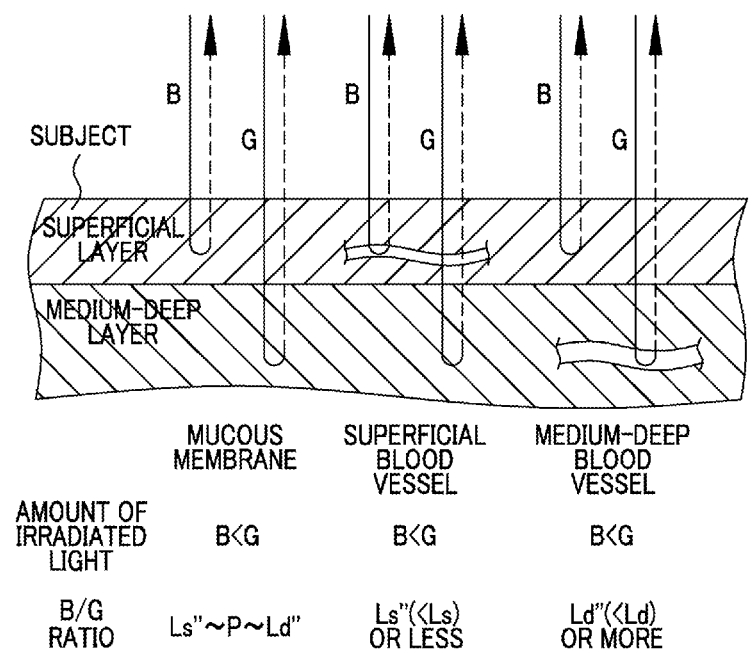
FIG. 10 is a diagram for explaining the B/G ratio when illumination light, in which the percentage of the G component is larger than the percentage of the B component, is irradiated to the mucous membrane, the superficial blood vessel, and the medium-deep blood vessel.

When the third observation mode is set, a superficial blood vessel extraction image or a medium-deep blood vessel extraction image is generated using a third light amount ratio table 63c that is suitable for the third light amount ratio in the third observation mode. As shown in FIG. 9, similar to the first light amount ratio table 63a, the third light amount ratio table 63c shows a proportional relationship in which the brightness ratio B/G (B/G ratio) increases as the blood vessel depth increases. In the third observation mode, as shown in FIG. 10, since the percentage of the green wavelength component (G component) of the illumination light is larger than the percentage of the blue wavelength component (B component) of the illumination light, the B/G ratio is generally low. Accordingly, a boundary value Ls" between the mucous membrane and the superficial blood vessel is smaller than the boundary value Ls in the first observation mode, and a boundary value Ld" between the mucous membrane and the medium-deep blood vessel is smaller than the boundary value Ld in the first observation mode.

Therefore, when generating a superficial blood vessel extraction image in the third observation mode, only the pixel value of a pixel having a B/G ratio equal to or less than Ls" is extracted from the B/G image, and binarization processing for setting the pixel values of other pixels to 0 is performed. On the other hand, when generating a medium-deep blood vessel extraction image, only the pixel value of a pixel having a B/G ratio equal to or greater than Ld" is extracted from the B/G image, and binarization processing for setting the pixel values of other pixels to 0 is performed.

The blood vessel enhancement image or suppression image generation section 65 generates a superficial blood vessel enhancement image or suppression image, in which a superficial blood vessel is enhanced (or suppressed), by combining the superficial blood vessel extraction image and the base image, and generates a medium-deep blood vessel enhancement image or suppression image, in which a medium-deep blood vessel is enhanced (or suppressed), by combining the medium-deep blood vessel extraction image and the base image. When enhancing the blood vessel, a value obtained by increasing the pixel value of each pixel in the superficial blood vessel extraction image (or a medium-deep blood vessel extraction image) several times is added to the pixel value of each pixel of the base image. When suppressing the blood vessel, a value obtained by increasing the pixel value of each pixel in the superficial blood vessel extraction image (or a medium-deep blood vessel extraction image) several times is subtracted from the pixel value of each pixel of the base image.

Figure 11:
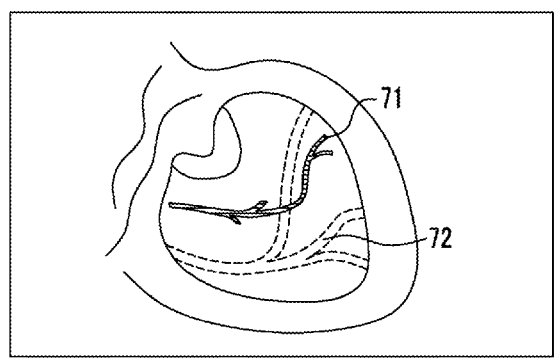
FIG. 11 is a diagram showing an image in which the superficial blood vessel is enhanced and the medium-deep blood vessel is suppressed.
Figure 12:
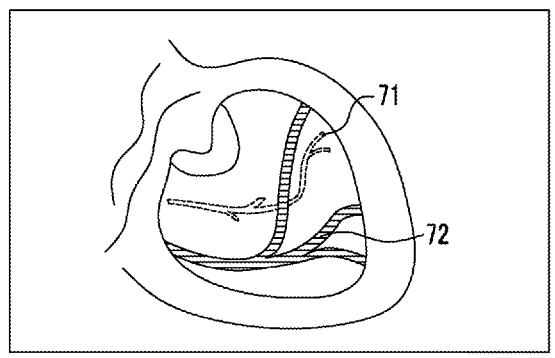
FIG. 12 is a diagram showing an image in which the superficial blood vessel is suppressed and the medium-deep blood vessel is enhanced.

The display control circuit 58 displays the blood vessel enhancement image or suppression image on the monitor 14 (a form of a display unit). For example, as shown in FIG. 11 when a superficial blood vessel 71 extracted from the B/G image is enhanced on the blood vessel enhancement image or suppression image, diagnosis focusing on only the superficial blood vessel 71 is possible since the superficial blood vessel 71 is noticeable compared with a medium-deep blood vessel 72. In contrast, as shown in FIG. 12, when the medium-deep blood vessel 72 extracted from the B/G image is enhanced on the blood vessel enhancement image or suppression image, diagnosis focusing on only the medium-deep blood vessel 72 is possible since the medium-deep blood vessel 72 is noticeable compared with the superficial blood vessel 71.

As described above, by extracting only an image of the blood vessel to be observed from the B/G image and generating a blood vessel enhancement image or suppression image using the extracted blood vessel image, only the blood vessel portion to be observed can be reliably enhanced/suppressed without eliminating the information of portions other than the blood vessel, for example, the information of unevenness of a part to be observed. Therefore, since not only the blood vessel information but also a lot of information useful for diagnosis, such as unevenness of a part to be observed, can be provided to the user, it is possible to improve the diagnostic performance. In addition, since blood vessels are divided into the superficial blood vessel and the medium-deep blood vessel so as to be separately extracted and each of the superficial blood vessel and the medium-deep blood vessel is separately enhanced/suppressed, diagnosis focusing on the superficial blood vessel or diagnosis focusing on the medium-deep blood vessel is possible.

Figure 13:
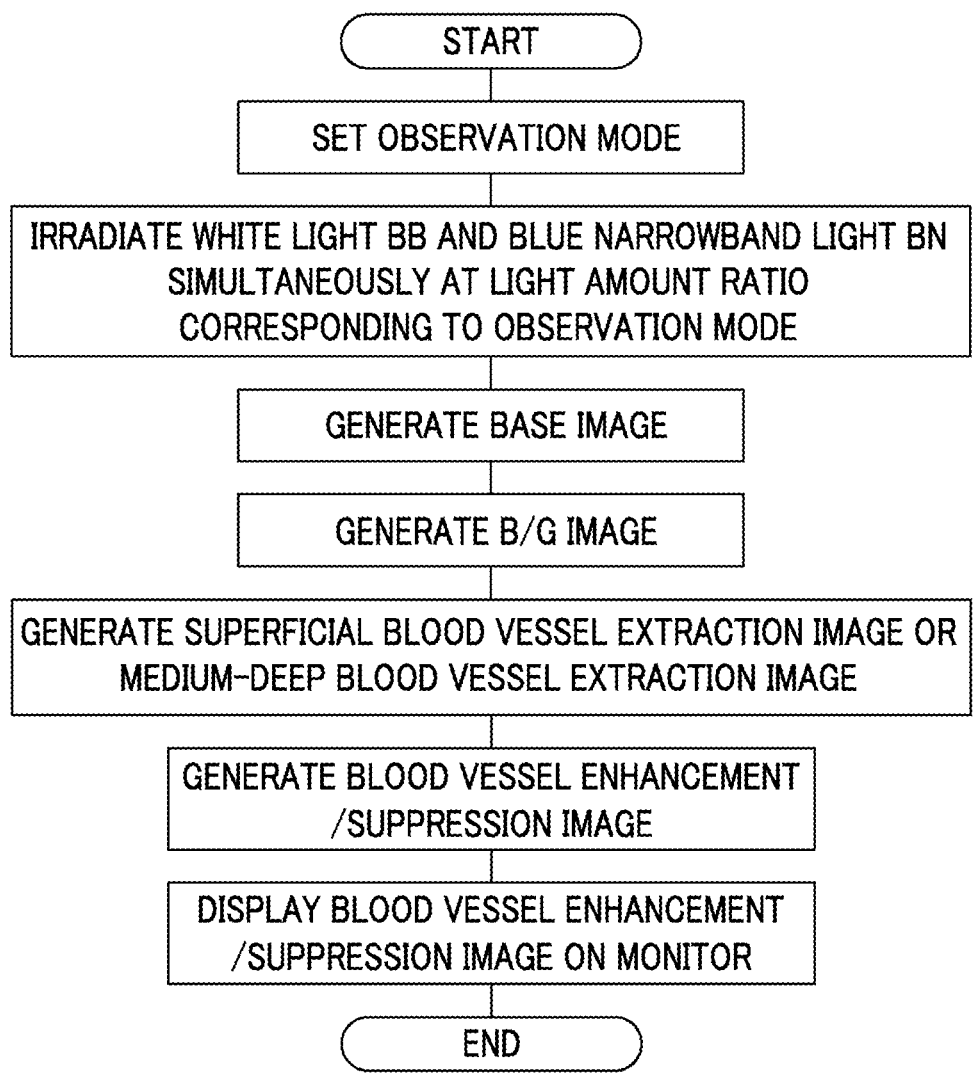
FIG. 13 is a flowchart showing the operation of one embodiment of the present invention.

Next, the operation of one embodiment of the present invention will be described with reference to the flowchart shown in FIG. 13. First, a predetermined observation mode of the first to third observation modes is set. Then, a light amount ratio (light amount ratio between the white light BB and the blue narrowband light BN) corresponding to the predetermined observation mode is set. The light amount of the white light BB and the blue narrowband light BN, which are emitted from the light source device 13 and are irradiated simultaneously into the subject through the light guide 43, is controlled so as to become the set light amount. Reflected light from the subject is imaged by the color CCD 44. A base image is generated from the blue signal B, the green signal G, and the red signal R obtained by this imaging. The generated base image, the blue signal B, the green signal G, and the red signal R are temporarily stored in the frame memory 56.

Then, the B/G image generation section 61 generates a B/G image having the brightness ratio B/G between the blue signal B and the green signal G A superficial blood vessel extraction image is generated by extracting the superficial blood vessel from the B/G image, and a medium-deep blood vessel extraction image is generated by extracting the medium-deep blood vessel from the B/G image. A light amount ratio table corresponding to the set light amount ratio is used for the blood vessel extraction. If the blood vessel extraction image is generated, a blood vessel enhancement image or suppression image in which a superficial blood vessel (or a medium-deep blood vessel) is enhanced/suppressed is generated from the superficial blood vessel extraction image (or the medium-deep blood vessel extraction image) and the base image. The generated blood vessel enhancement image or suppression image is converted into a signal, which can be displayed on a monitor, by the display control circuit 58 and is then image-displayed on the monitor 14 as shown in FIG. 11 or 12.

If the second observation mode is set in which the inside of the subject is observed with illumination light in which the percentage of the blue component is larger than the percentage of the green component, when generating an image for monitor display, it is preferable to assign the blue signal B of the image signals obtained by imaging to B and G channels of the video signal and assign the green signal G to an R channel of the video signal. In this case, a pseudo color image, in which the superficial blood vessel and the medium-deep blood vessel are displayed in different colors, is displayed on the monitor 14.

Figure 14:
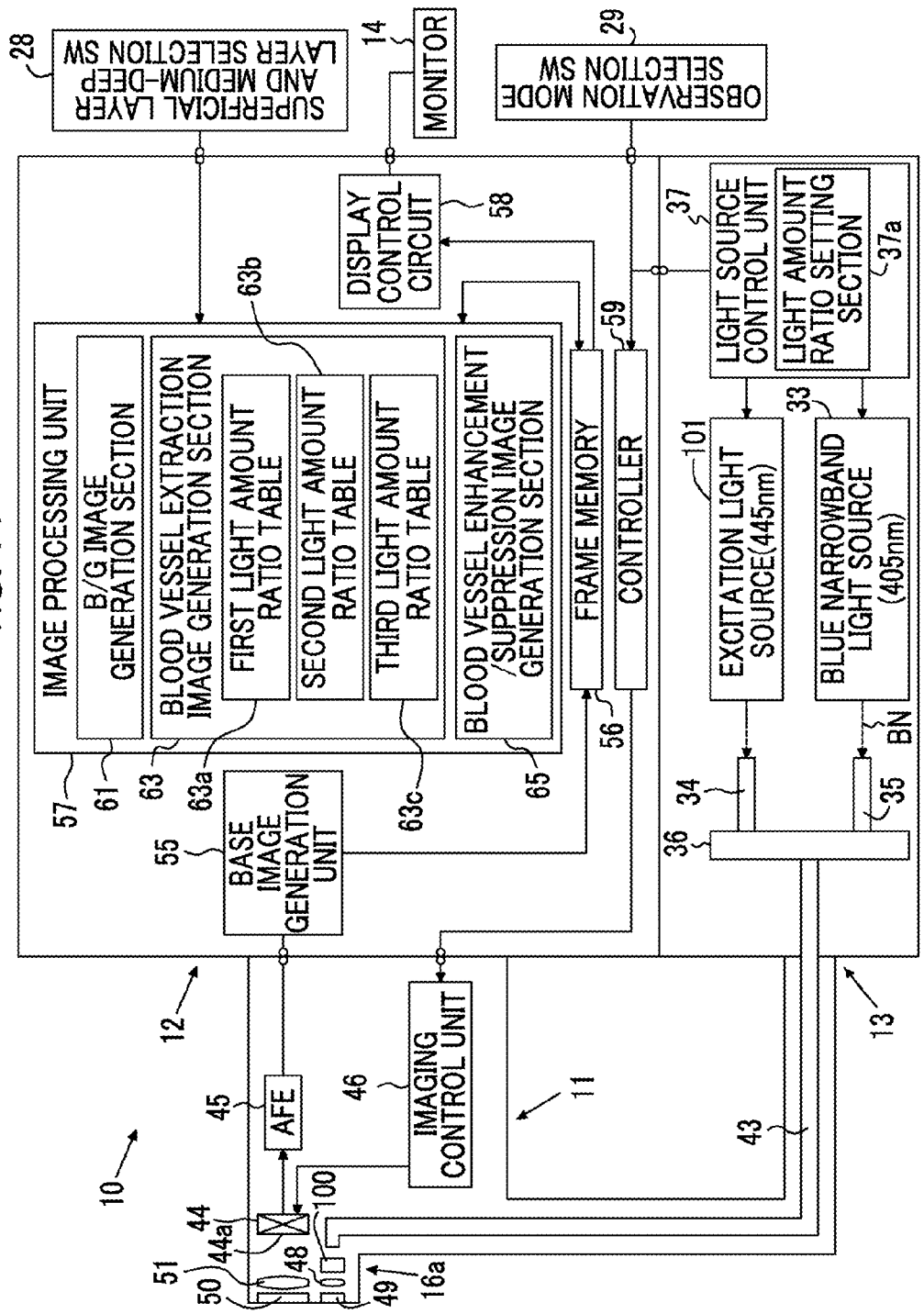
FIG. 14 is a block diagram showing the electrical configuration of an electronic endoscope system of an embodiment different from that in FIG. 2.

In the embodiment described above, the white light BB is emitted from the broadband light source 30 in the light source device 13. However, instead of this, fluorescent light may be emitted by providing a phosphor 100 in the distal portion 16a of the electronic endoscope 11 and exciting the phosphor 30b with excitation light from an excitation light source 101 provided in the light source device 13, as shown in FIG. 14. In this case, light obtained by combining the fluorescent light and excitation light, which is not absorbed by the phosphor 100, is irradiated into the subject as the white light BB. The phosphor 100 is the same as the phosphor 30b of the embodiment described above, and the excitation light source 101 is the same as the excitation light source 30a of the embodiment described above.

Figure 15:
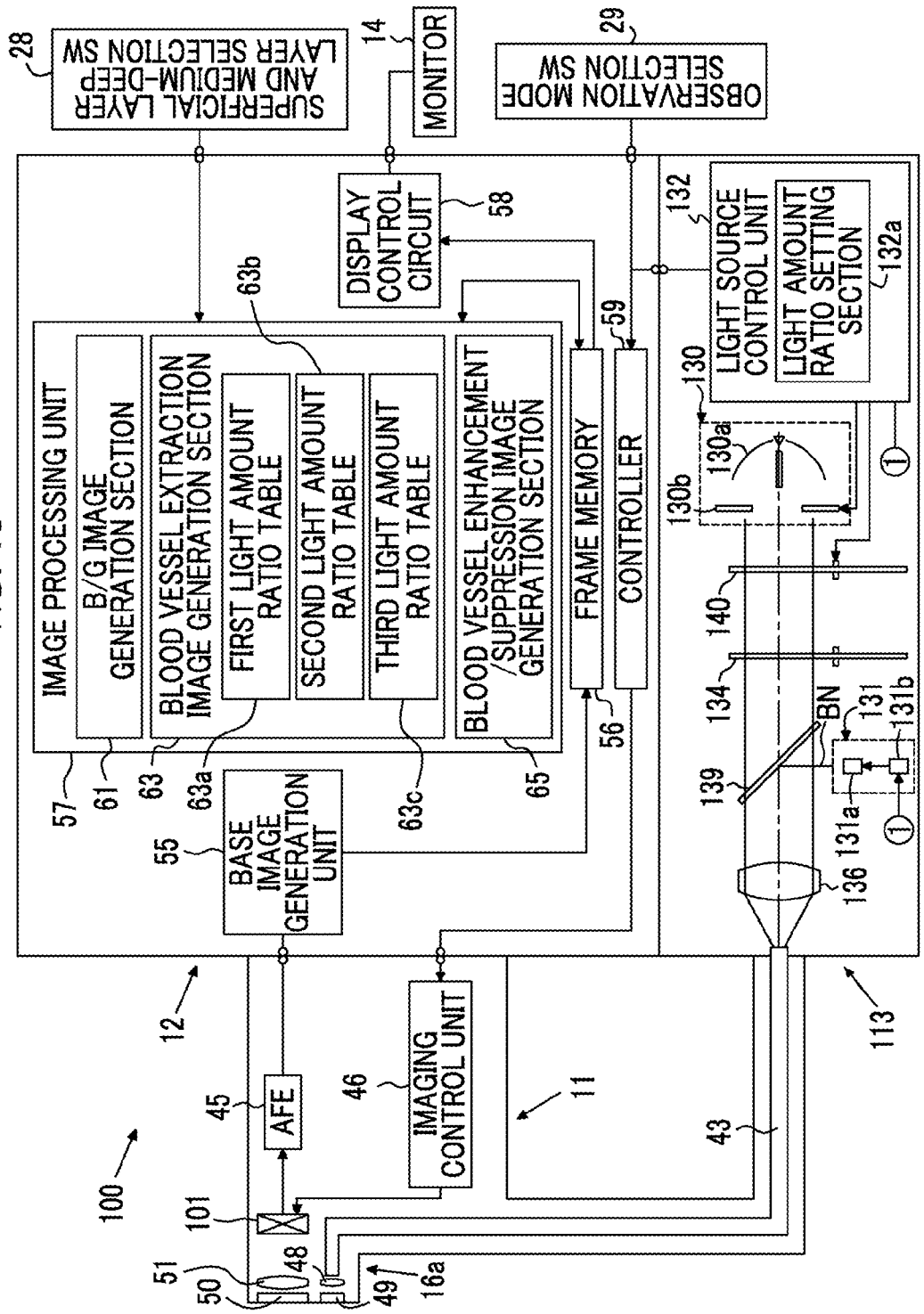
FIG. 15 is a block diagram showing the electrical configuration of an endoscope system of an embodiment different from those in FIGS. 2 and 14.

In addition, in the embodiment described above, the white light from the phosphor is irradiated into the subject. However, instead of this, some of a plurality of illumination light beams to illuminate the inside of the subject may be light from a semiconductor light source, and the other light beams may be light wavelength-separated from the white light of a xenon lamp or the like. In this case, for example, an electronic endoscope system 100 shown in FIG. 15 is used.

The electronic endoscope system 100 is different from the electronic endoscope system 10 in that an entire light source device 113 is different from the light source device 13 and a CCD 101 of an electronic endoscope 111 is a monochrome CCD. As observation modes, the electronic endoscope system 100 has a normal observation mode, in which the inside of the subject is observed with illumination light of three colors of blue light, green light, and red light, and first to third special observation modes, in which the inside of the subject is observed with illumination light of two colors of blue narrowband light and green light.

The light amount of the blue narrowband light and the light amount of the green light are different in the first to third special observation modes. In the first special observation mode, the light amount of the blue narrowband light and the light amount of the green light are equal. In the second special observation mode, the light amount of the blue narrowband light is larger than the light amount of the green light. In the third special observation mode, the light amount of the green light is larger than the light amount of the blue narrowband light. That is, the first to third special observation modes approximately correspond to the first to third observation modes of the embodiment described above. Therefore, blood vessel extraction methods in the first to third special observation modes are performed in the same manner as in the first to third observation modes. Since others are almost the same as in the embodiment described above, detailed explanation thereof will be omitted.

The light source device 113 includes a white light source unit 130, a semiconductor light source unit 131, and a light source control unit 132 that drives and controls them. The white light source unit 130 includes a lamp body 130a to emit the white light BB and an aperture 130b provided on the optical path of the lamp body 130a.

The lamp body 130a generates broadband light (white light) BB in which the emission spectrum is continuous in a wide wavelength range from a red region to a blue area (about 400 nm to 700 nm), like a xenon lamp, a halogen lamp, and a metal halide lamp. The lamp body 130a is always lit while the light source device 113 is ON. The degree of opening of the aperture 130b is adjusted by the driving control of the light source control unit 132. The light amount of the white light BB is adjusted by the adjustment of the degree of opening.

Figure 16:
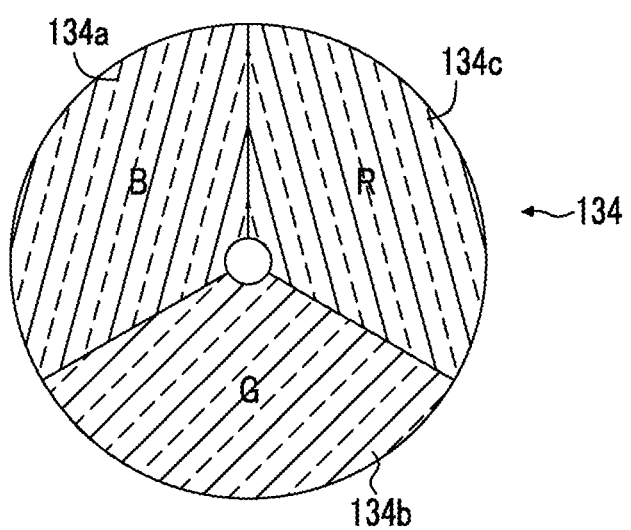
FIG. 16 is a diagram showing a rotary filter.

A rotary filter 134 is disposed on the optical path of the white light BB. As shown in FIG. 16, the rotary filter 134 has a disc shape, and is divided into three regions, each of which is a fan-shaped region having a central angle of 120°, in the circumferential direction, and a B filter portion 134a, a G filter portion 134b, and an R filter portion 134c through which light beams of B, G, and R are respectively transmitted are provided in the three regions.

Figure 17:
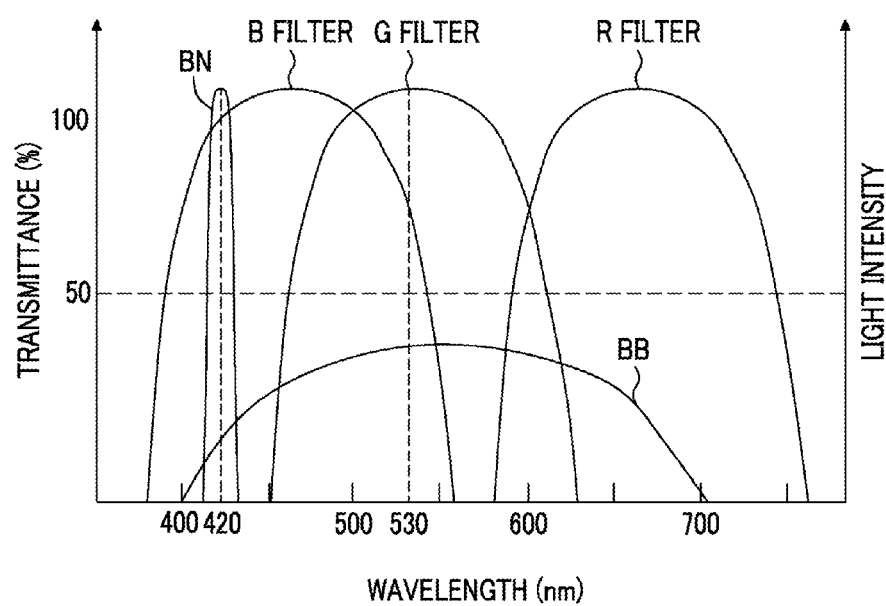
FIG. 17 is a graph showing the intensity distribution of blue narrowband light and the spectral transmittances of a B filter, a G filter, and an R filter of the rotary filter.

The B filter portion 134a, the G filter portion 134b, and the R filter portion 134c have spectral transmittances shown in FIG. 17. The B filter portion 134a allows blue light (B color light) of the white light BB to be transmitted therethrough, the G filter portion 134b allows green light (G color light) of the white light BB to be transmitted therethrough, and the R filter portion 134c allows red light (R color light) of the white light BB to be transmitted therethrough. Here, it is preferable that the transmission band of the G filter portion 134b be set such that the center wavelength of the G color light becomes 530 nm. Since the absorption coefficient of hemoglobin is high in a region near the wavelength of 530 nm, it is possible to increase the contrast between blood vessels and other parts by irradiating the blood vessels with light of this wavelength range.

The rotary filter 134 is rotatably provided so that the B filter portion 134a, the G filter portion 134b, and the R filter portion 134c are selectively inserted into the optical path of the white light BB. When the rotary filter 134 is rotated, the B filter portion 134a, the G filter portion 134b, and the R filter portion 134c are sequentially inserted into the optical path of the white light BB.

The semiconductor light source unit 131 includes a blue semiconductor light source 131a, which is a laser diode (LD) or a light emitting diode (LED), and a driving section 131b for driving the blue semiconductor light source 131a.

The blue semiconductor light source 131a emits the blue narrowband light BN having a center wavelength of 420 nm (refer to FIG. 17). Since the absorption coefficient of hemoglobin is high in a region near the wavelength of 420 nm, it is possible to increase the contrast between blood vessels and other parts by irradiating the blood vessels with light in this wavelength range.

The driving section 131b is connected to the light source control unit 132. The light source control unit 132 adjusts ON/OFF and the amount of light of the blue semiconductor light source 131a by controlling the driving section 131b. As a laser diode used for the blue semiconductor light source 131a, a broad area type InGaN-based laser diode, an InGaNAs-based laser diode, and a GaNAs-based laser diode can be used.

The B color light, the G color light, and the R color light from the rotary filter 134 and the blue narrowband light BN from the blue semiconductor light source 131a merge in a light merging section 139. The light merging section 139 is formed of a dichroic mirror, and allows the B color light, the G color light, and the R color light to be transmitted therethrough as they are and makes the blue narrowband light BN curved by 90° to merge into the optical path of the B color light, the G color light, and the R color light. The light transmitted through the light merging section 139 is incident on the light guide 43 through a condensing lens 136.

Figure 18:
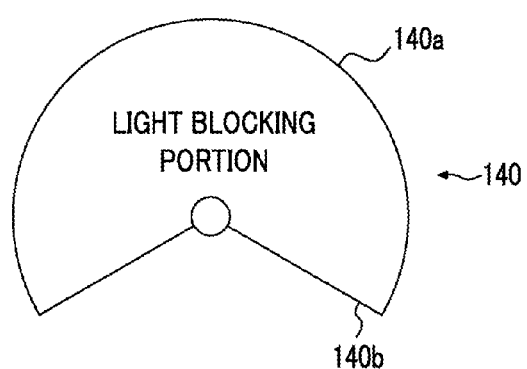
FIG. 18 is a diagram showing a shutter plate.

As shown in FIG. 15, a shutter plate 140 is disposed between the rotary filter 134 and the white light source unit 130. The shutter plate 40 blocks the white light BB when supplying the blue narrowband light BN to the electronic endoscope 11. As shown in FIG. 18, the shutter plate 140 is a member having a light blocking property for the white light BB, and its planar shape is a shape obtained by cutting a part of a circle.

Specifically, the shutter plate 140 has a light blocking portion 140a having a central angle of 240°, and the remaining 120° portion is cut to become a transmission portion 140b through which the white light BB is transmitted. The shutter plate 140 is rotatably provided, and the light blocking portion 140a and the transmission portion 140b are inserted alternately selectively into the optical path of the white light BB by rotation.

The shutter plate 140 has almost the same radius as the rotary filter 134, and the rotation axis matches that of the rotary filter 134. The central angle of the transmission portion 140b of the shutter plate 140 is almost the same as that of each of the B filter portion 134a, the G filter portion 134b, and the R filter portion 134c of the rotary filter 34. Although the transmission portion 140b is formed by cutting in this example, the transmission portion 140b may be formed of a transparent plate through which the white light BB is transmitted.

The rotation of the shutter plate 140 is controlled by the light source control unit 132. The rotation control changes with each observation mode. In the normal observation mode, the shutter plate 140 is stopped in a state where the light blocking portion 140a is retracted from the optical path of the white light BB and the transmission portion 140b is inserted into the optical path. Accordingly, the white light BB is always incident on the rotary filter 134. Along with this, light beams of three colors of B, G, and R colors are sequentially emitted from the rotary filter 134. In the normal observation mode, the blue semiconductor light source 13 is always OFF.

In contrast, in the first to third special observation modes, the shutter plate 140 rotates at the same speed as the rotary filter 134 so that the rotation phase of the transmission portion 140b and the rotation phase of the G filter portion 134b are the same. Accordingly, while the transmission portion 140h is inserted into the optical path of the white light BB and the light blocking portion 140a is retracted from the optical path, the white light BB is transmitted through the G filter portion 134b to generate G color light. The G color light is supplied to the electronic endoscope 11 after being transmitted through the condensing lens 136.

On the other hand, while the light blocking portion 140a is inserted into the optical path of the white light BB and the transmission portion 140b is retracted from the optical path, the white light BB is blocked. While the white light BB is blocked, the blue semiconductor light source 131a is turned on to supply the blue narrowband light BN to the electronic endoscope 11. Since the CCD 101 is a monochrome imaging element, color mixing of the white light BB and the blue narrowband light BN is prevented by providing the shutter plate 140.

As described above, the light source control unit 132 controls the degree of opening of the aperture 130b of the white light source unit 130 and the driving section 131b of the semiconductor light source unit 131. By this control, the light amount of the B color light, the G color light, and the R color light from the rotary filter 134 and the light amount of the blue narrowband light BN are adjusted. The light amount ratio between the G color light and the blue narrowband light BN used in the first to third special observation modes is set in advance for each of the special observation modes. As in the embodiment described above, the setting of the light amount ratio is performed by a light amount ratio setting section 132a. The light amount ratio setting section 132a sets a light amount ratio corresponding to the observation mode selected by the observation mode selection SW 29.

The first light amount ratio in the first special observation mode is set such that the light amount of the G color light is same as the light amount of the blue narrowband light BN. The second light amount ratio in the second special observation mode is set such that the light amount of the blue narrowband light BN is larger than the light amount of the G color light. The third light amount ratio in the third special observation mode is set such that the light amount of the G color light is larger than the light amount of the blue narrowband light BN.

In the electronic endoscope system 100, the monochrome CCD 101 and the rotary filter 134 are used. For this reason, the method of controlling the imaging of the CCD 101 and the based image generation method in a base image 55 are different from those in the case of the CCD 44 of the embodiment described above. In the normal observation mode, as shown in FIG. 19A, the CCD 101 performs an accumulation operation for accumulating signal charges and a read operation for reading the accumulated signal charges in an acquisition period of one frame. In the normal observation mode, image light beams of three colors of B, G, and R are sequentially captured, and the blue signal B, the green signal G, and the red signal R are sequentially output. Then, based on the signals B, and R of three colors, a base image is generated. The operations described above are repeatedly performed while the normal observation mode is set.

In contrast, in the first to third special observation modes, as shown in FIG. 19B, the blue signal B is sequentially output by capturing the image light of the blue narrowband light BN for a period of one frame of a period of two frames for which the blue narrowband light BN is irradiated into the subject. On the other hand, the green signal B is sequentially output by capturing the image light of the G color light for an irradiation period of one frame for which the G color light is irradiated into the subject. Then, based on the signals B and G of two colors, a base image is generated. The operations described above are repeatedly performed while the first to third special observation modes are set. In the first to third special observation mode, when generating a base image, it is preferable to assign the blue signal B to B and G channels for monitor display and assign the green signal G to an R channel for monitor display.

In the electronic endoscope system 100, in the first to third special observation modes, light of the semiconductor light source is used as the blue light, and light obtained by wavelength-separating the white light BB is used as the green light. In contrast, light of the semiconductor light source may be used as the green light, and light obtained by wavelength-separating the white light may be used as the blue light.

In the embodiment described above, medium-deep blood vessels and superficial blood vessels are separated from each other using the B/G ratio. Instead of this, the blood vessels can also be separated using calculation values obtained by calculation using two or more color signals having different pieces of color information, such as a G/B ratio, a B−G difference, a G−B difference, a B/(B+G) ratio, a G/(B+G) ratio, a B/R ratio, an R/B ratio, a B−R difference, an R−B difference, and a B/Y ratio.

Figure 20A:
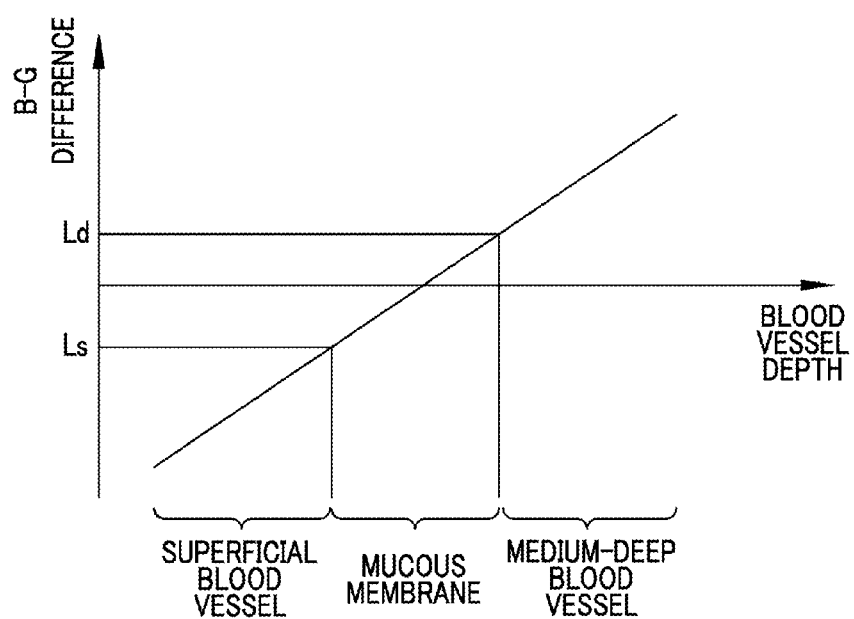
FIG. 20A is a graph showing the relationship between the blood vessel depth and the B−G difference that is stored in a first observation mode table.

As in the embodiment described above, the relationship between the calculated value and the blood vessel depth is stored in a plurality of tables corresponding to the first to third observation modes (first to third light amount ratios), and the boundary value of the calculated value indicating the boundary between the mucous membrane and the superficial blood vessel and the boundary value of the calculated value indicating the boundary between the mucous membrane and the medium-deep blood vessel differ depending on each table. For example, in the case of the B−G difference (a value obtained by subtracting the pixel value of the green signal from the pixel value of the blue signal), the relationship between the B−G difference and the blood vessel depth shown in FIG. 20A is stored in a table that is used in the first observation mode. Here, Ls indicates a B−G difference indicating the boundary between the mucous membrane and the superficial blood vessel, and Ld indicates a B−G difference indicating the boundary between the mucous membrane and the medium-deep blood vessel.

Figure 20B:
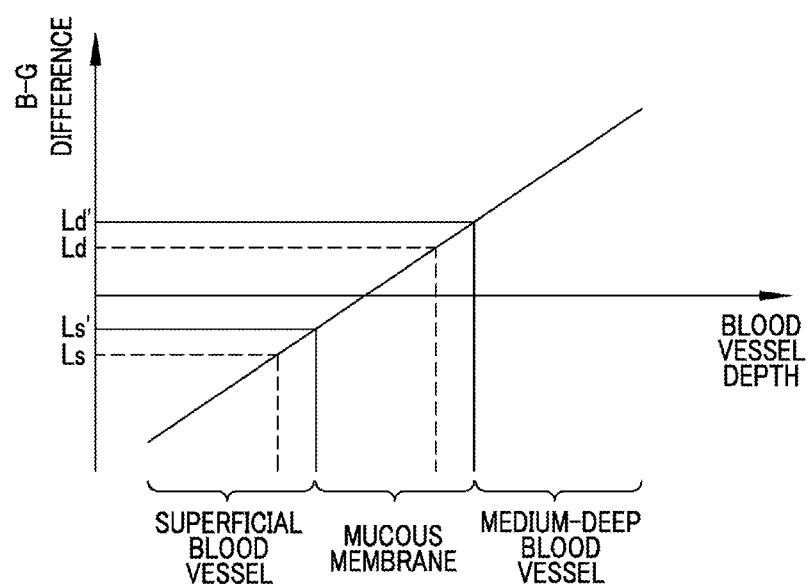
FIG. 20B is a graph showing the relationship between the blood vessel depth and the B−G difference that is stored in a second observation mode table.
Figure 20C:
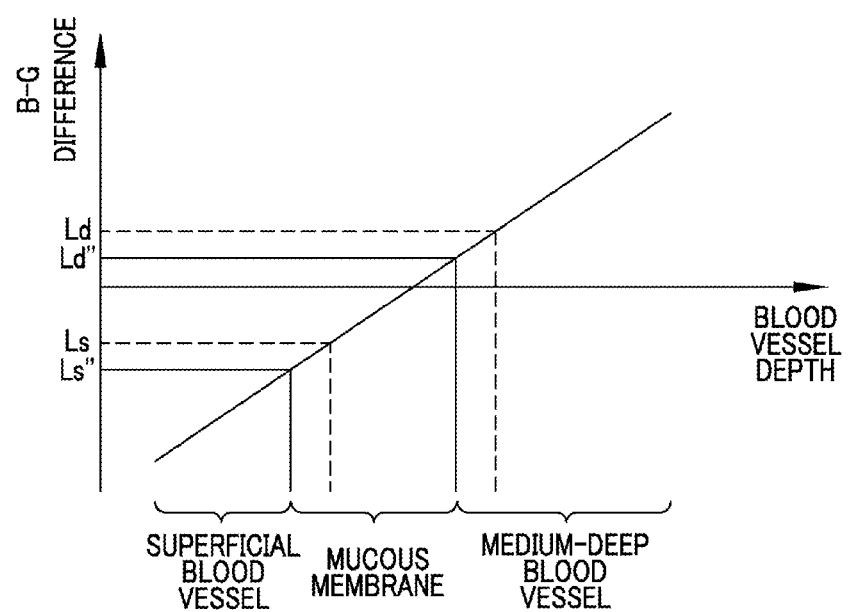
FIG. 20C is a graph showing the relationship between the blood vessel depth and the B−G difference that is stored in a third observation mode table.

On the other hand, the relationship between the B−G difference and the blood vessel depth shown in FIG. 20B is stored in a table that is used in the second observation mode. In this table, a B−G difference Ls' at the boundary between the mucous membrane and the superficial blood vessel is set to be larger than Ls, and a B−G difference Ld' at the boundary between the mucous membrane and the medium-deep blood vessel is set to be larger than Ld. In addition, the relationship between the B−G difference and the blood vessel depth shown in FIG. 20C is stored in a table that is used in the second observation mode. In this table, a B−G difference Ls" at the boundary between the mucous membrane and the superficial blood vessel is set to be smaller than Ls, and a B−G difference Ld" at the boundary between the mucous membrane and the medium-deep blood vessel is set to be smaller than Ld.

The G/B ratio is a value obtained by dividing the green signal by the blue signal, the B−G difference is a value obtained by subtracting the green signal from the blue signal, the G−B difference is a value obtained by subtracting the blue signal from the green signal, the B/(B+G) ratio is a value obtained by dividing the blue signal by the sum of the blue signal and the green signal, the G/(B+G) ratio is a value obtained by dividing the green signal by the sum of the blue signal and the green signal, the B/R ratio is a value obtained by dividing the blue signal by the red signal, the R/B ratio is a value obtained by dividing the red signal by the blue signal, the B−R difference is a value obtained by subtracting the red signal from the blue signal, the R−B difference is a value obtained by subtracting the blue signal from the red signal, and the B/Y ratio is a value obtained by dividing the green signal by the yellow signal (yellow signal is a signal having wavelength information of 500 nm to 700 nm).

What is claimed is:

1. An endoscope system, comprising:
a light source device that includes a light emitting unit, which emits two or more illumination light beams including first illumination light and second illumination light having different wavelength regions, and a light amount ratio setting unit, which sets a light amount ratio between the first illumination light and the second illumination light, and that irradiates a subject with the first illumination light and the second illumination light based on the light amount ratio set by the light amount ratio setting unit;
an electronic endoscope configured to acquire two or more color signals having different pieces of color information by receiving and imaging return light from the subject using an imaging element; and
a processor device that generates an endoscope image based on a signal obtained by imaging, wherein the processor device includes
a multi-color image generation unit configured to generate a multi-color image formed from calculated values obtained by performing predetermined calculation for each pixel using the two or more color signals; and
a blood vessel extraction image generation unit configured to generate at least one of a first layer blood vessel extraction image, which is obtained by extracting a first layer blood vessel at a specific depth from the multi-color image, and a second layer blood vessel extraction image, which is obtained by extracting a second layer blood vessel at a position deeper than the first layer blood vessel from the multi-color image, by performing blood vessel extraction processing, which differs depending on the light amount ratio, on the multi-color image.

2. The endoscope system according to claim 1,
wherein the light amount ratio setting unit sets one of a plurality of light amount ratios set in advance, and
the blood vessel extraction image generation unit includes a plurality of calculated value tables, which are set for the plurality of light amount ratios and which store a correlation between a mucous membrane, the first layer blood vessel, and the second layer blood vessel of the subject and the calculated values, and a blood vessel extraction image generation unit that generates at least one of the first layer blood vessel extraction image and the second layer blood vessel extraction image by performing blood vessel extraction processing using a calculated value table corresponding to the light amount ratio set by the light amount ratio setting unit.

3. The endoscope system according to claim 2,
wherein, in each of the calculated value tables, a calculated value indicating a boundary between the mucous membrane and the first layer blood vessel is stored as a first boundary value, and a calculated value indicating a boundary between the mucous membrane and the second layer blood vessel is stored as a second boundary value, and
the first and second boundary values differ depending on each calculated value table.

4. The endoscope system according to claim 3, further comprising:
a blood vessel enhancement image or suppression image generation unit for generating a first layer blood vessel enhancement image or suppression image, in which the first layer blood vessel is enhanced or suppressed, using the first layer blood vessel extraction image or generating a second layer blood vessel enhancement image or suppression image, in which the second layer blood vessel is enhanced or suppressed, using the second layer blood vessel extraction image.

5. The endoscope system according to claim 4, further comprising:
a display unit for displaying at least one of the first layer blood vessel enhancement image or suppression image and the second layer blood vessel enhancement image or suppression image.

6. The endoscope system according to claim 3,
wherein light source device irradiates first illumination light, which includes blue excitation light and fluorescent light that is wavelength-converted by a wavelength conversion member using the blue excitation light, and second illumination light, which has a wavelength region in which a center wavelength is on a short wavelength side compared with the excitation light, simultaneously toward the subject, and
the electronic endoscope images the subject, to which the first illumination light and the second illumination light are irradiated simultaneously, using a color imaging element.

7. The endoscope system according to claim 2, further comprising:
a blood vessel enhancement image or suppression image generation unit for generating a first layer blood vessel enhancement image or suppression image, in which the first layer blood vessel is enhanced or suppressed, using the first layer blood vessel extraction image or generating a second layer blood vessel enhancement image or suppression image, in which the second layer blood vessel is enhanced or suppressed, using the second layer blood vessel extraction image.

8. The endoscope system according to claim 7, further comprising:
a display unit for displaying at least one of the first layer blood vessel enhancement image or suppression image and the second layer blood vessel enhancement image or suppression image.

9. The endoscope system according to claim 2,
wherein the light source device irradiates first illumination light, which includes blue excitation light and fluorescent light that is wavelength-converted by a wavelength conversion member using the blue excitation light, and second illumination light, which has a wavelength region in which a center wavelength is on a short wavelength side compared with the excitation light, simultaneously toward the subject, and
the electronic endoscope images the subject, to which the first illumination light and the second illumination light are irradiated simultaneously, using a color imaging element.

10. The endoscope system according to claim 1,
wherein the light source device irradiates first illumination light, which includes blue excitation light and fluorescent light that is wavelength-converted by a wavelength conversion member using the blue excitation light, and second illumination light, which has a wavelength region in which a center wavelength is on a short wavelength side compared with the excitation light, simultaneously toward the subject, and
the electronic endoscope images the subject, to which the first illumination light and the second illumination light are irradiated simultaneously, using a color imaging element.

11. The endoscope system according to claim 10,
wherein the wavelength conversion member is provided in a separate light source device from an endoscope that irradiates the first illumination light and the second illumination light toward the subject.

12. The endoscope system according to claim 11,
wherein a center wavelength of the excitation light is 445 nm, and a center wavelength of the second illumination light is 405 nm.

13. The endoscope system according to claim 10,
wherein the wavelength conversion member is provided at a distal end of an endoscope that irradiates the first illumination light and the second illumination light toward the subject.

14. The endoscope system according to claim 10,
wherein a center wavelength of the excitation light is 445 nm, and a center wavelength of the second illumination light is 405 nm.

15. The endoscope system according to claim 1, further comprising:
a blood vessel enhancement image or suppression image generation unit for generating a first layer blood vessel enhancement image or suppression image, in which the first layer blood vessel is enhanced or suppressed, using the first layer blood vessel extraction image or generating a second layer blood vessel enhancement image or suppression image, in which the second layer blood vessel is enhanced or suppressed, using the second layer blood vessel extraction image.

16. The endoscope system according to claim 15, further comprising:
a display unit for displaying at least one of the first layer blood vessel enhancement image or suppression image and the second layer blood vessel enhancement image or suppression image.

17. The endoscope system according to claim 1,
wherein the first illumination light is illumination light having a center wavelength of 420 nm, and the second illumination light is illumination light having a center wavelength of 530 nm.

18. The endoscope system according to claim 1,
wherein the color signals include a blue signal having information of a blue component and a green signal having information of a green component, and
the multi-color image is a B/G image having a B/G ratio obtained by dividing the blue signal by the green signal for each pixel.

19. A processor device for an endoscope system according to claim 1 including a light source device, which includes a light emitting unit that emits two or more illumination light beams including first illumination light and second illumination light having different wavelength regions and a light amount ratio setting unit that sets a light amount ratio between the first illumination light and the second illumination light, and which irradiates a subject with the first illumination light and the second illumination light based on the light amount ratio set by the light amount ratio setting unit, and an electronic endoscope configured to acquire two or more color signals having different pieces of color information by receiving and imaging return light from the subject using an imaging element, the processor device comprising:
a multi-color image generation unit for generating a multi-color image formed from calculated values obtained by performing predetermined calculation for each pixel using the two or more color signals; and
a blood vessel extraction image generation unit for generating at least one of a first layer blood vessel extraction image, which is obtained by extracting a first layer blood vessel at a specific depth from the multi-color image, and a second layer blood vessel extraction image, which is obtained by extracting a second layer blood vessel at a position deeper than the first layer blood vessel from the multi-color image, by performing blood vessel extraction processing, which differs depending on the light amount ratio, on the multi-color image.

20. An image processing method performed in an endoscope system according to claim 1 including a light source device, which includes a light emitting unit that emits two or more illumination light beams including first illumination light and second illumination light having different wavelength regions and a light amount ratio setting unit that sets a light amount ratio between the first illumination light and the second illumination light and which irradiates a subject with the first illumination light and the second illumination light based on the light amount ratio set by the light amount ratio setting unit, and an electronic endoscope configured to acquire two or more color signals having different pieces of color information by receiving and imaging return light from the subject using an imaging element, and a processor device that generates an endoscope image based on a signal obtained by imaging the image processing method comprising:
generating a multi-color image formed from calculated values obtained by performing predetermined calculation for each pixel using the two or more color signals by using the processor device; and
generating at least one of a first layer blood vessel extraction image, which is obtained by extracting a first layer blood vessel at a specific depth from the multi-color image, and a second layer blood vessel extraction image, which is obtained by extracting a second layer blood vessel at a position deeper than the first layer blood vessel from the multi-color image, by performing blood vessel extraction processing, which differs depending on the light amount ratio, on the multi-color image, by using the processor device.

* * * * *